US010206620B2

(12) United States Patent
Camacho Perez et al.

(10) Patent No.: US 10,206,620 B2
(45) Date of Patent: Feb. 19, 2019

(54) USER'S PHYSIOLOGICAL CONTEXT MEASUREMENT METHOD AND APPARATUS

(71) Applicant: Intel Corporation, Santa Clara, CA (US)

(72) Inventors: Jose Rodrigo Camacho Perez, Guadalajara Jalisco (MX); Paulo Lopez Meyer, Zapopan (MX); Alejandro Ibarra Von Borstel, Tlajomulco (MX); Julio Cesar Zamora Esquivel, Zapopan (MX); Hector Alfonso Cordourier Maruri, Guadalajara (MX)

(73) Assignee: Intel Corporation, Santa Clara, CA (US)

( * ) Notice: Subject to any disclaimer, the term of this patent is extended or adjusted under 35 U.S.C. 154(b) by 70 days.

(21) Appl. No.: 15/078,746

(22) Filed: Mar. 23, 2016

(65) Prior Publication Data

US 2017/0273621 A1 Sep. 28, 2017

(51) Int. Cl.
*A61B 5/01* (2006.01)
*A61B 5/00* (2006.01)
(Continued)

(52) U.S. Cl.
CPC .............. *A61B 5/6803* (2013.01); *A61B 5/01* (2013.01); *A61B 5/0803* (2013.01);
(Continued)

(58) Field of Classification Search
CPC ....... A61B 5/6803; A61B 5/01; A61B 5/0803; A61B 5/0816; A61B 5/72;
(Continued)

(56) References Cited

U.S. PATENT DOCUMENTS 4,520,238 A 5/1985 Ikeda
6,285,211 B1 9/2001 Sample et al.
(Continued)

FOREIGN PATENT DOCUMENTS

CN 101742387 A 6/2010
JP 03121603 A 5/1991
(Continued)

OTHER PUBLICATIONS

International Search Report issued in PCT Application No. PCT/US2016/047206, dated Oct. 27, 2016, 12 pages.
(Continued)

*Primary Examiner* — Paula J Stice
(74) *Attorney, Agent, or Firm* — Schwabe, Williamson & Wyatt, P.C.

(57) ABSTRACT

Embodiments of the present disclosure provide techniques and configurations for an apparatus for a user's physiological context measurements. In one instance, the apparatus may include a head-fitting component to be mounted at least partly around a user's head, and a sensor disposed on the head-fitting component to generate a signal indicative of a user's physiological context in response to contact with the user's head. The physiological context may comprise a respiration cycle, and the sensor may sense vibration in a portion of the user's head produced in response to the respiration cycle. The apparatus may further include a controller coupled with the sensor, to process the signal and generate data indicative of the physiological context of the user. Other embodiments may be described and/or claimed.

12 Claims, 11 Drawing Sheets

(51) Int. Cl.
  *A61B 5/08*  (2006.01)
  *A61B 17/00*  (2006.01)
(52) U.S. Cl.
  CPC ............. *A61B 5/0816* (2013.01); *A61B 5/72* (2013.01); *A61B 2017/0011* (2013.01); *A61B 2560/045* (2013.01); *A61B 2562/0271* (2013.01)
(58) Field of Classification Search
  CPC ...... A61B 2017/0011; A61B 2560/045; A61B 2562/0271
  USPC ................................................ 600/529, 534
  See application file for complete search history.

(56) References Cited

U.S. PATENT DOCUMENTS

| | | | |
|---|---|---|---|
| 7,789,837 | B2 | 9/2010 | Lehrman et al. |
| 8,856,875 | B2 | 10/2014 | Aditya |
| 2005/0286734 | A1 | 12/2005 | Wang |
| 2006/0000472 | A1 | 1/2006 | Fenton |
| 2006/0140422 | A1 | 6/2006 | Zurek et al. |
| 2007/0109491 | A1* | 5/2007 | Howell .................. G02C 11/10 351/41 |
| 2009/0018419 | A1 | 1/2009 | Torch |
| 2010/0110368 | A1 | 5/2010 | Chaum |
| 2010/0331649 | A1 | 12/2010 | Chou |
| 2011/0224481 | A1 | 9/2011 | Lee et al. |
| 2011/0308323 | A1 | 12/2011 | Oizumi |
| 2012/0197737 | A1 | 8/2012 | LeBoeuf et al. |
| 2012/0282976 | A1 | 11/2012 | Suhami |
| 2013/0063550 | A1 | 3/2013 | Ritchey et al. |
| 2013/0159705 | A1 | 6/2013 | Leedom, Jr. |
| 2013/0242262 | A1 | 9/2013 | Lewis |
| 2014/0028546 | A1 | 1/2014 | Jeon et al. |
| 2014/0029762 | A1 | 1/2014 | Xie et al. |
| 2014/0275852 | A1 | 9/2014 | Hong et al. |
| 2014/0378113 | A1 | 12/2014 | Song et al. |
| 2015/0031964 | A1 | 1/2015 | Bly et al. |
| 2015/0074797 | A1 | 3/2015 | Choi et al. |
| 2015/0135310 | A1 | 5/2015 | Lee |
| 2015/0160622 | A1 | 6/2015 | Kim et al. |
| 2015/0185838 | A1 | 7/2015 | Camacho-Perez et al. |
| 2015/0265161 | A1* | 9/2015 | Hernandez ............. A61B 5/024 600/476 |
| 2015/0289820 | A1 | 10/2015 | Miller et al. |
| 2016/0070245 | A1 | 3/2016 | Lee et al. |
| 2016/0091980 | A1 | 3/2016 | Baranski et al. |
| 2016/0246368 | A1 | 8/2016 | Camacho-Perez et al. |
| 2016/0282945 | A1 | 9/2016 | Ochoa |
| 2016/0284135 | A1 | 9/2016 | Zamhi |
| 2016/0378193 | A1 | 12/2016 | Rodrigo |
| 2017/0075426 | A1 | 3/2017 | Camacho Perez et al. |
| 2017/0078464 | A1 | 3/2017 | Cordourier Maruri et al. |
| 2017/0078788 | A1 | 3/2017 | Meyer |
| 2017/0090583 | A1 | 3/2017 | Zamora Esquivel et al. |

FOREIGN PATENT DOCUMENTS

| | | |
|---|---|---|
| KR | 20110068579 A | 6/2011 |
| KR | 10-2012-0080852 A | 7/2012 |
| KR | 10-2013-0035290 A | 4/2013 |
| WO | 2015123771 A1 | 8/2015 |

OTHER PUBLICATIONS

Tamura,Toshiyo, et al.,: "Wearable Photoplethysmographic Sensors—Past and Present", Electronics, No. 3, 2014, pp. 282-302, DOI:10.3390/electronics3020282.
H. Han, J_ Kim, "Artifacts in wearable photoplethysmographs during daily life motions and their reduction with least mean square based active noise cancellation method", Computers in biology and medicine, 42(4), Apr. 2012, pp. 387-393, Abstract only.
K.F. Teng, Y.T. Zhang, "The effect of contacting force on photoplethysmographic signals", Physiological Measurement, No. 25, Aug. 11, 2004, pp. 1323-1335, Abstract only.
B. Park, C.R. Farrar, A. C. Rutherford, A.N. Robertson, "Piezo-Sensor Self-Diagnostics Using Electrical Impedance measurements", Los Alamos National Laboratory, Technical Report LA-UR-04, Oct. 24-27, 2004, 17 pages.
Myo Armband, hllps://www.thalmic.com/myo, downloaded Mar. 22, 2017, 5 pages.
Chianura, A., et al.: "Electrooptical muscle contraction sensor", Medical & biological engineering & computing, 48(7), pp. 731-734, Jul. 2010, 12 pages.
Raghavendra, J.: "Optomyography: detection of muscle surface displacement using reflective photo resistor", MSc. Thesis, KTH Technology and Health, Stockholm, Aug. 2014, pp. 1-31.
Cheng, E.Y., et al: "Forehead pulse oximetry compared with finger pulse oximetry and arterial blood gas measurement", Journal of Clinical Monitoring, Jul. 4, 1988, vol. 4, Issue 3, pp. 223-226, Abstract only.
Barry, D.T., et al.: "Acoustic myography as a control signal for an externally powered prosthesis", Archives of Physical Medicine and Rehabilitation, vol. 67, No. 4, Apr. 1986, pp. 267-269, Abstract only.
Overly, T.G., et al: "Piezoelectric active-sensor diagnostics and validation using instantaneous baseline data", IEEE Sensors Journal, vol. 9, No. 11, Nov. 2009, pp. 1414-1421, Abstract only.
Jim, J. M., et al: "Recognizing hand gestures using wrist shapes". In Consumer Electronics {ICCE), 2010 Digest of Technical Papers International Conference, IEEE, Jan. 2010, pp. 197-198, Abstract only.
Alian, A. A., et al: "Photoplethysmography." Best Practice & Research Clinical Anaesthesiology, 28(4), Dec. J014, pp. 395-406, Abstract only.
Mason, W.P., et al.: "Methods for Measuring Piezoelectric, Elastic, and Dielectric Coefficients of Crystals and : eramics", Proceedings of the IRE.vol. 42, Jun. 6, 1954, 1 page, Abstract only.
Harrison, Chris, et al.: "Skinput: Appropriating the Body as an Input Surface", http://www.chrisharrison.net/index.php/Research/Skinput, downloaded Mar. 22, 2017, 10 pages.
Hakansson et al., "Resonance Frequencies of the Human Skull in Vivo Department of Applied Electronics", Chalmers University of Technology, Gothenburg, Sweden, Nov. 12, 1993.
Carter, et al., "Estimation of the Magnitude-Squared Coherence Function Via Overlapped Fast Fourier Transform Processing", IEEE Transactions on Audio and Electroacoustics, vol. AU-21, No. 4, Aug. 1973.
Piezoelectric Sound Components, muRata catalogue, May 2014.
Welch, "The Use of Fast Fourier Transform for the Estimation of Power Spectra: A Method Based on Time Averaging Over Short, Modified Periodograms", IEEE Transactions on Audio and Electroacoustics, vol. AU-15, No. 2, Jun. 1967.
International Search Report and Written Opinion issued in PCT Application No. PCT/US2016/047089, dated Oct. 26, 2016.
Office Action issued in U.S. Appl. No. 14/854,927, dated Sep. 1, 2016.
International Search Report and Written Opinion issued in PCT Application No. PCT/US2016/061420, dated Jan. 18, 2017, 15 pages.
U.S. Office Action issued in U.S. Appl. No. 14/965,095, dated Oct. 21, 2016.
Final Office Action issued in U.S. Appl. No. 14/965,095, dated May 2, 2017, 21 pages.
Non-Final Office Action dated Apr. 5, 2017, issued in related U.S. Appl. No. 14/855,746, 16 pages.
Final Office Action dated Sep. 13, issued in related U.S. Appl. No. 14/855,746, 16 pages.
U.S. Appl. No. 14/854,927, entitled "System for Voice Capture Via Nasal Vibration Sensing," filed Sep. 15, 2015.
U.S. Appl. No. 14/965,095, entitled "System for Voice Capture Via Nasal Vibration Sensing," filed Dec. 10, 2015.
U.S. Appl. No. 14/855,746, entitled "Techniques for Gesture Recognition Using Photoplethysmographic (PPMG) Sensor and Low-Power Wearable Gesture Recognition Device Using the Same," filed Sep. 16, 2015.

(56) References Cited

OTHER PUBLICATIONS

Tarrant, C., S., et al, "Comparative Review of Techniques for Recording Respiratory Events at Rest and During Deglutition", Dysphagia, vol. 12, No. 1, pp. 24-38, 1997.
Reichert, S., et al., "Analysis of Respiratory Sounds: State of the Art," Clin Med Circ Respirat Pulm Med., May 16, 2008; 2:45-58.
Moussavil, Z., K., et al., "Automated Detection of Respiratory Phases by Acoustical Means," IEEE EMBS 1998, vol. 20, No. 1 ,1998.
Nam, Y., et al., Respiration Rate Estimation from the Built-In Cameras of Smartphones and Tablets, Annals of Biomedical Engineering Apr. 2014, vol. 42, Issue 4, pp. 885-898.
Li, X., "Using Mobile Phone Sensors to Detect Rapid Respiratory Rate in the Diagnosis of Pneumonia," International Journal of Engineering and Technology ,vol. 8, No. 4, Apr. 2016.
Klap, T., et al.,"Using Piezoelectric Sensor for Continuous-Contact-Free Monitoring of Heart and Respiration Rates in Real-Life Hospital Settings," Computing in Cardiology 2013; 40:671-674.
Jeong, J. W., et al., "Wearable Respiratory Rate Monitoring Using Piezo-resistive Fabric Sensor," WC 2009, IFMBE Proceedings 25/V pp. 282-284, 2009.
Shrout, P.E., et al., "Intraclass Correlations: Uses in Assessing Rater Reliability," Psychol Bull. Mar. 1979;86(2):420-8.
International Search Report and Written Opinion, dated May 18, 2017, issued in related International Application No. PCT/US2017/018235, 15 pages.

\* cited by examiner

USER'S PHYSIOLOGICAL CONTEXT MEASUREMENT METHOD AND APPARATUS

FIELD

Embodiments of the present disclosure generally relate to the field of wearable devices, and more particularly, to wearable devices also configured to measure a user's physiological context.

BACKGROUND

Portable or wearable devices continue to increase in popularity, and feature increasingly sophisticated functionality, including wireless capabilities. Some of the devices may be used to measure a user's physiological context, such as parameters related to the user's health, for example, respiration cycle, heart rate, temperature, or the like. For example, smartphones have been proposed to be used as photoplethysmography devices. However, using a mobile device for physiological context measurement may require the user to perform a particular action, such as placing a finger on a display of the mobile device, placing the mobile device on the user's chest for a period of time to perform necessary measurements, or the like. Accordingly, physiological context measurements may require user involvement and take the user's time away from other tasks to be performed on a device.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example and not by way of limitation in the figures of the accompanying drawings.

DETAILED DESCRIPTION

Embodiments of the present disclosure include techniques and configurations for an apparatus and method for a user's physiological context measurements. In some embodiments, the apparatus may include a head-fitting component to be mounted at least partly around a user's head, and a sensor disposed on the head-fitting component to generate a signal indicative of a user's physiological context in response to contact with the user's head. The physiological context may comprise a respiration cycle, and the sensor may sense vibration in a portion of the user's head produced in response to the respiration cycle. The apparatus may further include a controller coupled with the sensor, to process the signal and generate data indicative of the physiological context of the user.

In the following detailed description, reference is made to the accompanying drawings that form a part hereof, wherein like numerals designate like parts throughout, and in which are shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), (A) or (B), or (A and B). For the purposes of the present disclosure, the phrase "A, B, and/or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment" or "in embodiments," which may each refer to one or more of the same or different embodiments. Furthermore, the terms "comprising," "including," "having," and the like, as used with respect to embodiments of the present disclosure, are synonymous.

The term "coupled with," along with its derivatives, may be used herein. "Coupled" may mean one or more of the following. "Coupled" may mean that two or more elements are in direct physical, electrical, or optical contact. However, "coupled" may also mean that two or more elements indirectly contact each other, but yet still cooperate or interact with each other, and may mean that one or more other elements are coupled or connected between the elements that are said to be coupled with each other. The term "directly coupled" may mean that two or more elements are in direct contact.

Figure 1:
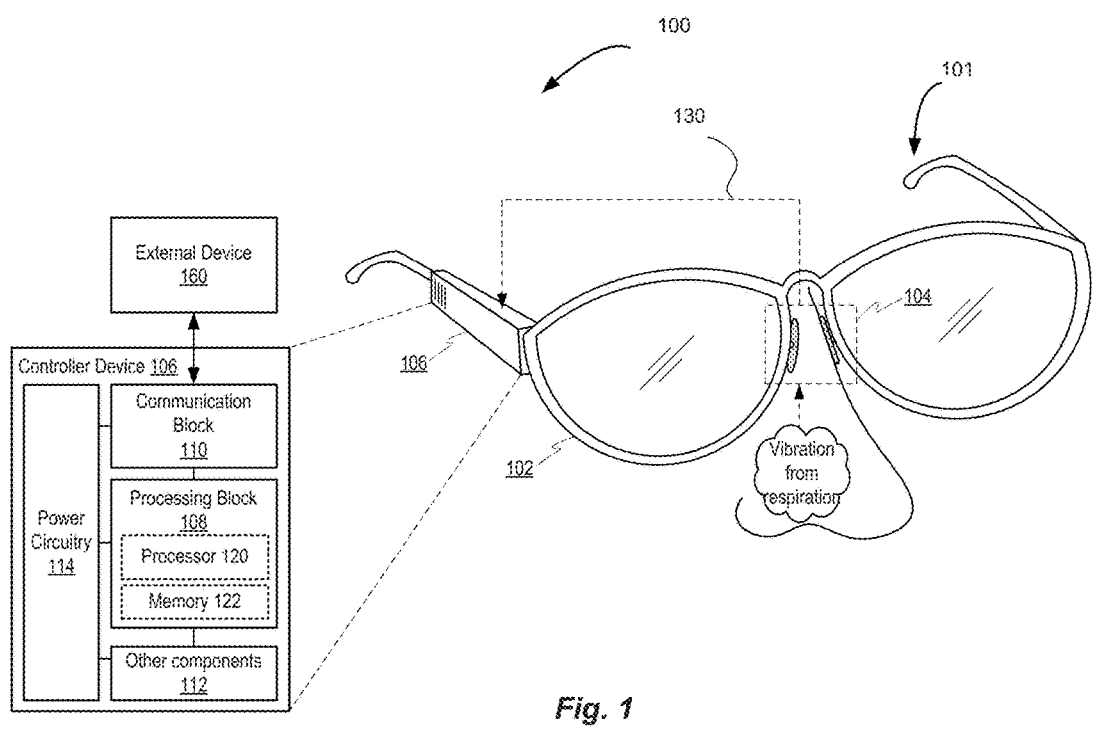
FIG. 1 is a diagram illustrating an example apparatus for a user's physiological context measurements incorporated with the teachings of the present disclosure, in accordance with some embodiments.

FIG. 1 is a diagram illustrating an example apparatus for a user's physiological context measurements incorporated with the teachings of the present disclosure, in accordance with some embodiments. The apparatus 100 may comprise a wearable device, to be worn on or around a user's head. Example implementations may include eyeglasses, helmets, headsets, diadems, caps, hats, or other types of headwear. While examples of specific implementations (e.g., in eyeglasses) and/or technologies (e.g., piezoelectric sensors, wireless communications, etc.) may be employed herein, these examples are presented merely to provide a readily comprehensible perspective from which the more generalized devices, methods, etc. described herein may be understood.

As noted above, the apparatus 100 may comprise a wearable device, such as eyeglasses 101, in the example illustrated in FIG. 1. The apparatus 100 may include a body, such as frame 102 of eyeglasses 101. The frame 102 is described herein as a part of the apparatus 100 (in this example, eyeglasses 101) for the sake of explanation. Other applications or configurations of an apparatus 100 may result in implementations that remain consistent with the teachings presented herein.

At least one sensor 104 may be disposed on the apparatus 100, such as on the frame 102, as shown in FIG. 1. For example, the sensor 104 may be mounted on the frame 102 via mechanical attachment (e.g., screw, nail or other fastener), adhesive attachment (e.g., a glue, epoxy, etc.) or may be incorporated within the structure of the frame 102. In embodiments, the sensor 104 may comprise vibration sensing circuitry. The sensing circuitry may comprise, for example, piezoelectric components such as a diaphragm or other piezoelectric transducer, to convert vibration (e.g., mechanical pressure waves) occurring in portions of the user's head into signals.

As shown, the sensor 104 may be disposed on the frame 102 to be in contact with, or at least proximate to, the nose of a user wearing the apparatus 100. The bridge of the user's nose may resonate in response to the user's respiration, such as inhaling and exhaling. The sensor 104 may be able to detect vibration caused by the nasal bones resonating with the user's respiration, and may convert the sensed vibration into a signal 130, e.g., an electronic signal, to be processed as described below. The embodiments of this disclosure are not limited to nasal vibration detection described above and are described herein for ease of understanding. Other types of vibration indicative of the user's respiration cycle may be sensed in different portions of the user's head, such as, for example, temples, forehead, or other portions of the user's head, and more specifically, in the upper portion of the user's head. These embodiments will be described in greater detail below.

The apparatus 100 may further include a controller device 106, which may also be disposed on the apparatus 100 (e.g., the frame 102) as shown. The controller device 106 may be electrically and/or communicatively coupled with the sensor 104, to receive and process the signal 130 provided by the sensor 104, and to generate data indicative of the physiological context of the user, such as respiration or temperature, as described below.

The controller device 106 may comprise, for example, a processing block 108, to process the signal 130 and generate data indicative of the physiological context of the user, and communication block 110 to transmit the data to an external device 160. The processing block 108 may comprise at least a processor 120 and memory 122. The processing block 108 may include components configured to record and process the readings of the signal 130. The processing block 108 may provide these components through, for example, a plurality of machine-readable instructions stored in the memory 122 and executable on the processor 120. The controller device 106 may record the signal 130 and store (e.g., buffer) the recorded readings, for example, in the memory 122, for further analysis and processing, e.g., in real time or near-real time.

The processor 120 may include, for example, one or more processors situated in separate components, or alternatively one or more processing cores embodied in a component (e.g., in a System-on-a-Chip (SoC) configuration), and any processor-related support circuitry (e.g., bridging interfaces, etc.). Example processors may include, but are not limited to, various microprocessors including those in the Pentium®, Xeon®, Itanium®, Celeron®, Atom®, Quark®, Core® product families, or the like.

Examples of support circuitry may include host side or input/output (I/O) side chipsets (also known as northbridge and southbridge chipsets/components) to provide an interface through which the processor 120 may interact with other system components that may be operating at different speeds, on different buses, etc. in device 106. Some or all of the functionality commonly associated with the support circuitry may also be included in the same physical package as the processor.

The memory 122 may comprise random access memory (RAM) or read-only memory (ROM) in a fixed or removable format. RAM may include volatile memory configured to hold information during the operation of device 106 such as, for example, static RAM (SRAM) or Dynamic RAM (DRAM). ROM may include non-volatile (NV) memory circuitry configured based on basic input/output system (BIOS), Unified Extensible Firmware Interface (UEFI), etc. to provide instructions when device 106 is activated, programmable memories such as electronic programmable ROMs (erasable programmable read-only memory), Flash, etc. Other fixed/removable memory may include, but is not limited to, electronic memories such as solid state flash memory, removable memory cards or sticks, etc.

The communication block 110 may be communicatively coupled with external device 160 and may include one or more radios capable of transmitting and receiving signals using various suitable wireless communications techniques. Such techniques may involve communications across one or more wireless networks. Some example wireless networks include (but are not limited to) wireless local area networks (WLANs), wireless personal area networks (WPANs), wireless metropolitan area network (WMANs), cellular networks, and satellite networks. In communicating across such networks, the communication block 110 may operate in accordance with one or more applicable standards in any version. To this end, the communication block 110 may include, for instance, hardware, circuits, software, or any combination thereof that allows communication with external computer systems.

In some specific non-limiting examples, the communication block 110 may comport with the Institute of Electrical and Electronics Engineers (IEEE) 802.11 standard (e.g., Wi-Fi), a Bluetooth®, ZigBee®, near-field communication, or any other suitable wireless communication standard. In addition, the communication block 110 may comport with cellular standards such as 3G (e.g., Evolution-Data Optimized (EV-DO), Wideband Code Division Multiple Access (W-CDMA)) and/or 4G wireless standards (e.g., High Speed Packet Access (HSPA), Worldwide Interoperability for Microwave Access (WIMAX), Long-Term Evolution (LTE)).

The apparatus 100 may further include a power circuitry block 114 configured to provide power supply to the components of the controller device 106. In some embodiments, the power circuitry block 114 may be configured to power on the controller device 106 continuously or periodically, in order to save battery power. In some embodiments, the power circuitry block 114 may be configured to power on the controller device 106 on a "wake-up" basis, e.g., in response to vibration detection by the sensor 104. The power circuitry block 114 may include internal power sources (e.g., battery, fuel cell, etc.) and/or external power sources (e.g., power grid, electromechanical or solar generator, external fuel cell, etc.) and related circuitry configured to supply device 106 with the power needed to operate.

The controller device 106 may include other components 112 that may be necessary for functioning of the apparatus 100. Other components 112 may include, for example, hardware and/or software to allow users to interact with the controller device 106 such as, for example, various input mechanisms (e.g., microphones, switches, buttons, knobs, keyboards, speakers, touch-sensitive surfaces, one or more sensors configured to capture images and/or sense proximity, distance, motion, gestures, orientation, biometric data, etc.) and various output mechanisms (e.g., speakers, displays, lighted/flashing indicators, electromechanical components for vibration, motion, etc.). The hardware in other components 112 may be incorporated within the controller device 106 and/or may be external to the device 106 and coupled to device 106 via a wired or wireless communication medium.

Figure 2:
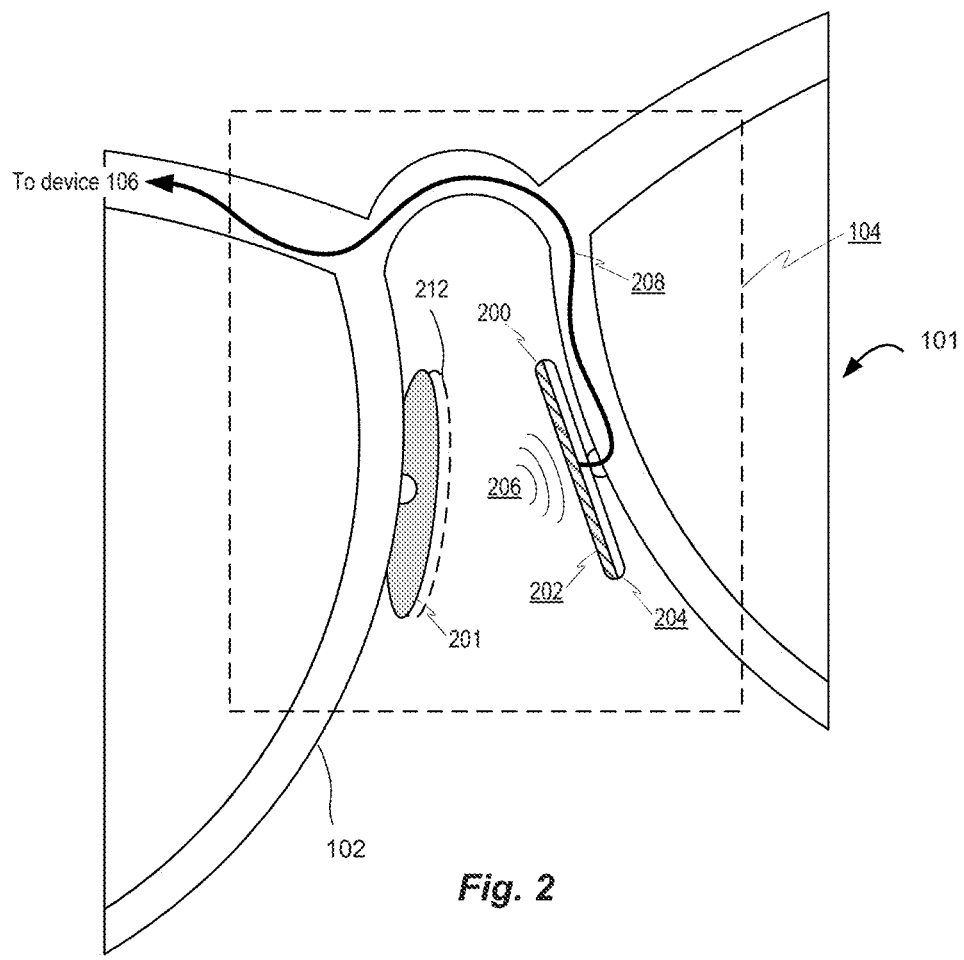
FIG. 2 illustrates an example configuration of the apparatus of FIG. 1, in accordance with some embodiments.

FIG. 2 illustrates an example configuration of the apparatus of FIG. 1, in accordance with some embodiments. More specifically, FIG. 2 illustrates an example disposition of the sensing circuitry in the frame 102 of the apparatus 100. For ease of understanding, like elements of FIGS. 1 and 2 are indicated by like numerals. As shown, the sensor 104 may be disposed within a nosepiece 200 of the frame 102. The sensor 104 may comprise, for example, sensing circuitry (e.g., piezoelectric transducer) 202 affixed or removably attached to structural support 204 of the nosepiece 200 of the frame 102. The sensing circuitry 202 may include, for example, a piezoelectric diaphragm to convert vibration 206 into a signal. Vibration 206 may occur due to the user's nasal bones (not shown) that may resonate in response to the user's respiration. The piezoelectric diaphragm comprising the sensing circuitry 202 may be able to accurately generate a signal indicative of respiration and may not require external power, because the pressure waves may compress a piezoelectric crystal of the diaphragm to generate the electronic signal.

The eyeglasses 101 may further include a wire 208 to convey the signal from the sensor 104 to the controller device 106. The wire 208 is shown for illustration purposes; the use of wireless communication may also be possible to transmit the signal to the controller device 106.

A variety of sensor configurations may be implemented consistent with the present disclosure. For example, given that two nosepieces 200 and 201 may exist in a common pair of glasses, at least one of the two nosepieces 200, 201 may include the sensor 104. In another example implementation, both nosepieces 200 and 201 may include sensing circuitries 202 and 212 (shown in dashed lines), comprising the sensor 104. For example, the circuitries 202 and 212 disposed in each nosepiece 200 may be wired in series to generate stronger signals. In another embodiment, the circuitries 202, 212 in the nosepieces 200, 201 may be wired individually, and the controller device 106 (e.g., processing block 108) may select the sensor circuitry 202 or 212 of the sensor 104 to employ based on the strength of the electronic signals received from each sensor circuitry. In this manner, the apparatus 100 may be able to account for the particularities in each user's nasal bones (e.g., breaks, natural deformities such as a deviated septum, etc.) and select the particular sensor circuitry that may provide the strongest and cleanest signal.

The embodiments of FIGS. 1 and 2 describe the apparatus for the user's physiological context measurements adapted for eyewear. Eyewear such as eyeglasses, sunglasses, safety glasses, or the like are routinely worn by people. Accordingly, the embodiments described herein may be easily adopted in the day-to-day life of a user. As noted above, other embodiments configured to measure the user's physiological context may be contemplated, some of which are described in reference to FIG. 3.

Figure 3:
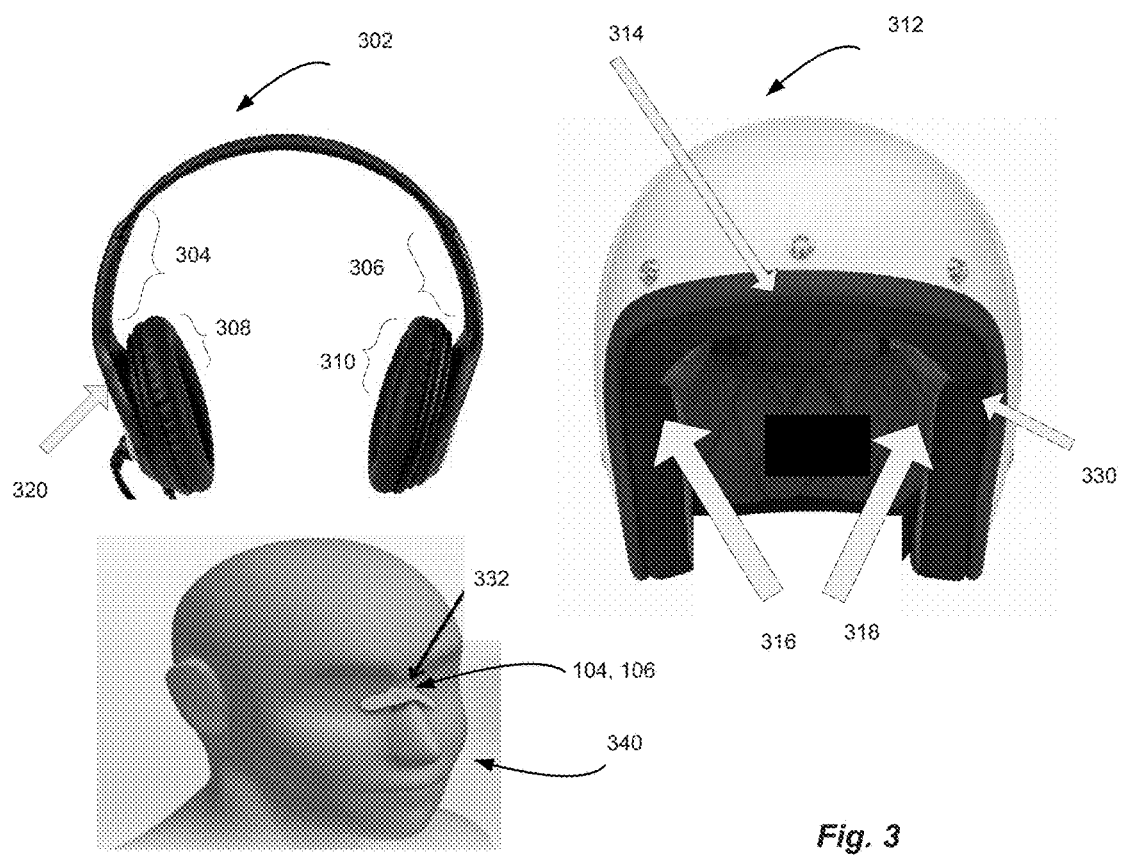
FIG. 3 illustrates some example embodiments of an apparatus for the user's physiological context measurements, in accordance with some embodiments.

FIG. 3 illustrates some example embodiments of an apparatus for the user's physiological context measurements, in accordance with some embodiments. In example embodiments, the apparatus may comprise a wearable device, such as a headset 302 or a helmet 312. The sensors, such as the sensor 104, may be disposed in different areas of the headset 302 and helmet 312, as indicated by numerals 304, 306, 308, and 310; and 314, 316, and 318 respectively. In general, the sensors may be disposed such as to provide a contact (e.g., direct contact or proximity contact) between the sensors and an upper portion of the user's head in response to application of the wearable device 302 or 312 to the user's head. As shown, the sensors may be disposed in a head-fitting area of a respective wearable device in order to provide the contact between the sensors and the temples or forehead of the user, to conduct sensing of the respective bone vibration in response to the user's inhaling and exhaling.

In embodiments, the controller device (e.g., 106) may also be mounted on the wearable device 302 or 312, as indicated by numerals 320 and 330 respectively. As described above, the device 106 and the sensor (or sensors) 104 may be communicatively coupled to enable signal transmission from the sensors to the controller device. Understandably, the controller device may be mounted in other suitable areas of a respective wearable device, depending on the wearable device configuration.

As noted, other types of wearable devices configured to provide the user's physiological context measurements may include, but may not be limited to, diadems, caps, hats, or other types of headwear. In general, any headwear or form factors that may provide for contact of a sensor with an upper portion of the user's head may be used with embodiments described herein.

In some embodiments, form factors may include patch-like implementation 332 applied to the user's nasal bones, as shown in example view 340. The patch-like implementation 332 may include the sensor 104 with associated electronics (e.g., controller device 106), for use, for example, in sleep studies (e.g., sleep apnea detection tests), where eyeglasses or other headwear may not be suitable for the task.

Figure 4:
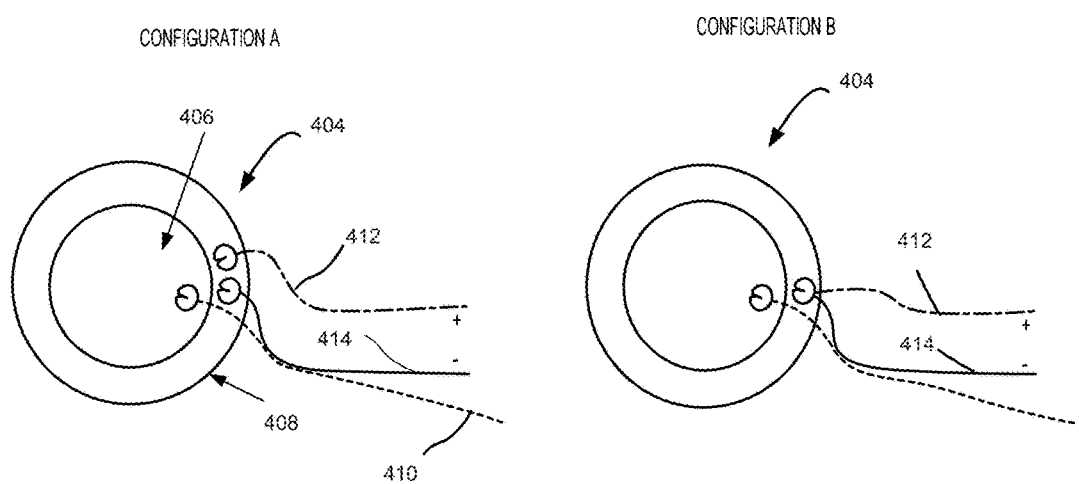
FIG. 4 illustrates example sensors that may be used in an apparatus for the user's physiological context measurement, in accordance with some embodiments.

FIG. 4 illustrates example sensors that may be used in an apparatus for the user's physiological context measurement, in accordance with some embodiments. The example sensors are shown in configurations A and B, described below in greater detail.

As shown, for example, in configuration A, a sensor 404 may comprise a piezoelectric sensor and include a piezoelectric diaphragm (crystal) 406 to provide signal (output voltage) in response to sensing a vibration. The piezoelectric crystal 406 may be coupled to (e.g., disposed inside) a metal disk 408 that may provide the ground for the resulting circuit. The wires 410 and 412 connected to the crystal 406 and the ground 408 respectively may provide the piezoelectric signal (output voltage) of the sensor 404.

In some embodiments, one of the electrical contacts of the disk 408 (e.g., wires 410 or 412) may be replaced with a thermocouple. The thermocouple may be in close contact with the nose bone (or other portions of the head of the user as described above), and may provide for measurements of the user's temperature in addition to measurements of respiration described above. Accordingly, the addition of a thermocouple to the piezoelectric sensor may enable continuous body temperature monitoring.

The advantages of the described embodiments may include utilizing form factors naturally compatible to many wearable devices, such as ones described in reference to FIGS. 1-3. The described sensor embodiments may require a minimum amount of low-cost additional hardware (one regular thermocouple and a simple voltage monitoring circuit). No complex or power consuming sensors or processing algorithms may be required. Further, the temperature measurements may provide a desired precision, as evidenced by graphs in FIG. 5 showing experimental results of temperature measurements.

With reference to FIG. 4, configuration A further illustrates the sensor 404 with an added thermocouple. The thermocouple may include two wires 412 and 414 soldered apart on the metal disk 408. In configuration B, the sensor 404 may include the thermocouple with wires 412 and 414 that may be soldered together in the metal disk 408. One of the wires from the thermocouple (e.g., wire 412) may serve as a common ground for the sensor 404, which may reduce the number of wires coming from the sensor.

Figure 5:
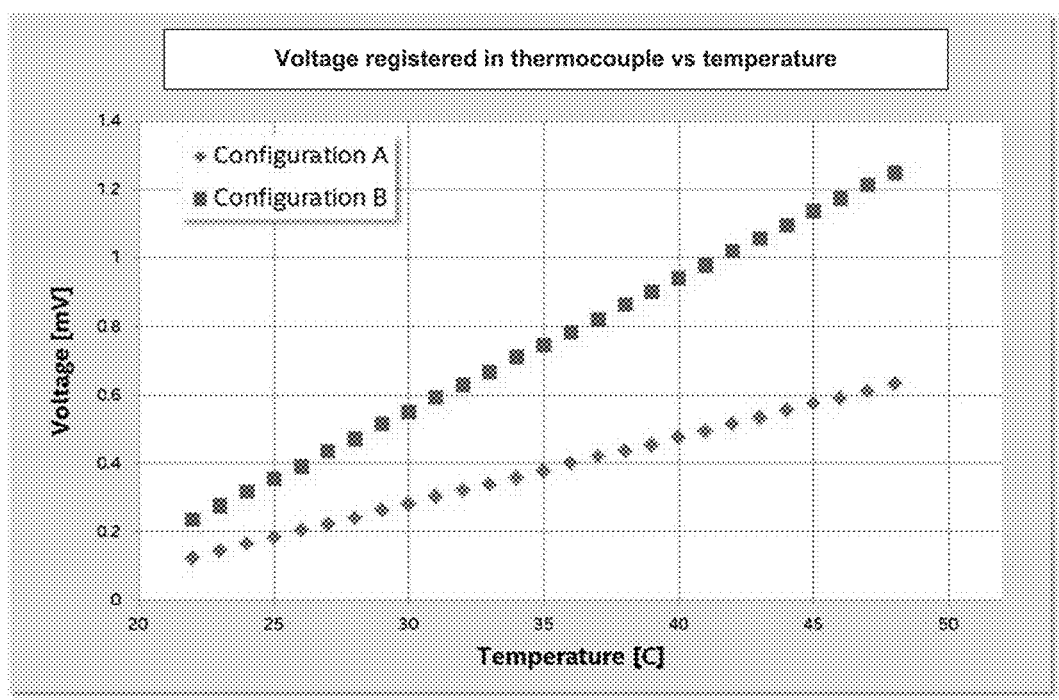
FIG. 5 illustrates a graph showing test results of the example sensor in different configurations, in accordance with some embodiments.

FIG. 5 illustrates a graph showing test results of the example sensor 404 in different configurations, in accordance with some embodiments. As can be seen, both sensor configurations A and B may provide a linear correlation between temperature and output voltage signal provided by the thermocouple. As shown, configuration B may provide a higher output compared to configuration A, and may be more suitable for some implementations. As shown in the graphs of FIG. 5, a thermocouple attached to the piezoelectric disk may detect, in general, any regular temperature in contact with the disk 408, and in particular the user's body temperature range (e.g., 35°-41° C., or 95°-106° F.).

Figure 6:
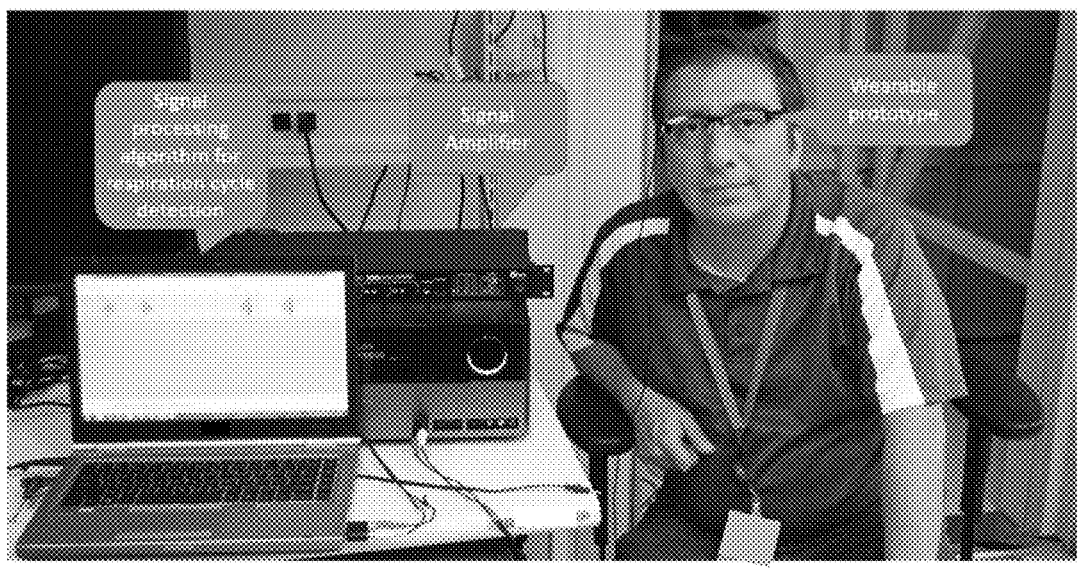
FIG. 6 is an example experimental setup for testing an apparatus for the user's physiological context measurements, in accordance with some embodiments.

FIG. 6 is an example experimental setup for testing an apparatus for the user's physiological context measurements, in accordance with some embodiments. For experimental purposes, two sensors (piezoelectric transducers) fabricated as described in reference to FIGS. 1-5 may be connected in series. Each sensor may be composed of a metallic disk and a thin layer of piezoelectric material (Murata® 7BB-20-6L0), as described in reference to FIG. 4. The sensors may be mounted on the nasal support of a pair of commercially available glasses, similar to the embodiments described in reference to FIGS. 1-2. A test subject is shown as wearing the prototype eyeglasses comprising the apparatus for the user's physiological context measurements. The test subject may breathe normally for a finite period of time, e.g., 60 sec. The resulting number of complete inhale and exhale periods may equal 21, with a complete number of 10 respiration cycles per minute.

Figure 7:
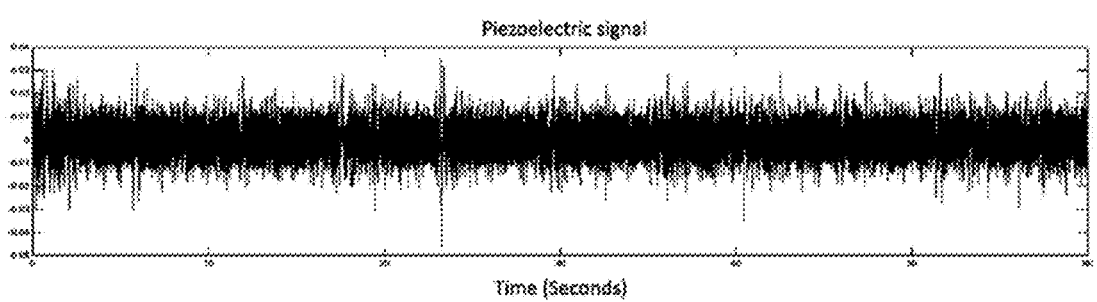
FIG. 7 is a graph illustrating an example representation of the electronic (piezoelectric) signal captured during testing on the experimental setup of FIG. 6, in accordance with some embodiments.

FIG. 7 is a graph illustrating an example representation of the electronic (e.g., piezoelectric) signal captured during testing on the experimental setup of FIG. 6, in accordance with some embodiments. The signal may be recorded at a sample frequency of 41 kHz, and down sampled to 16 kHz for post-processing analysis. The timing of the signal (shown on X-axis) may be divided into 250 ms non-overlapping windows ti (for i=1, 2, . . . , n number of windows) to obtain a spectrogram Si using the short-time Fourier transform, as described below.

Figure 8:
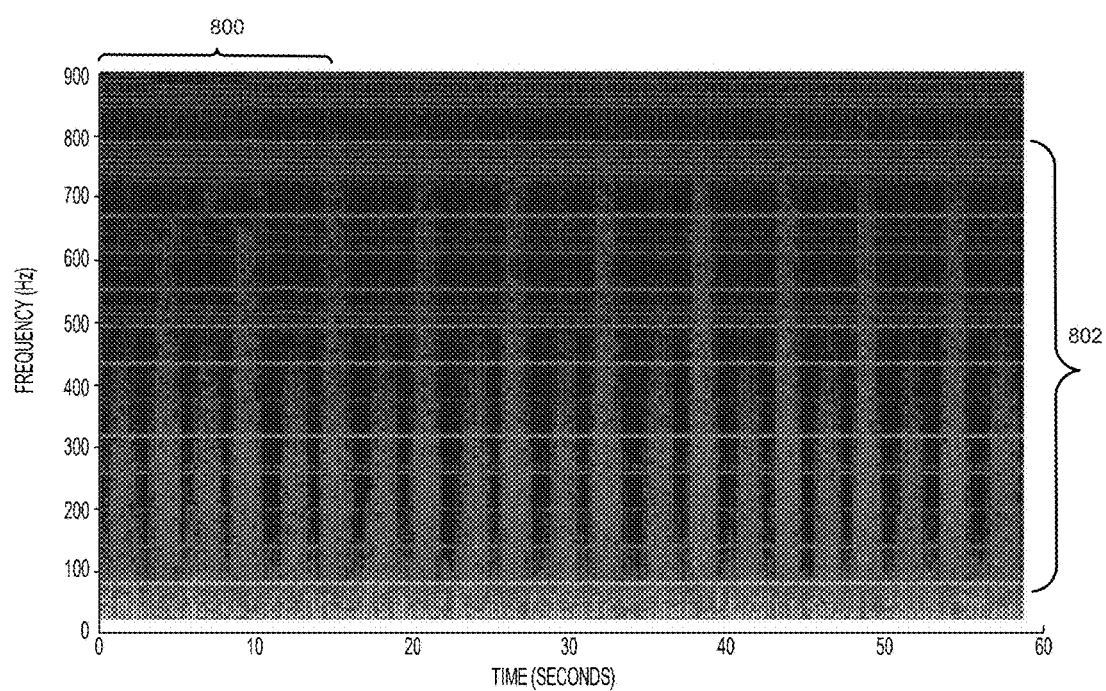
FIG. 8 is a graph illustrating an example spectrogram based on the electronic (piezoelectric) signal captured during testing on the experimental setup of FIG. 6, in accordance with some embodiments.

FIG. 8 is a graph illustrating an example spectrogram based on the electronic (piezoelectric) signal captured during testing on the experimental setup of FIG. 6, in accordance with some embodiments. The portion of the spectrogram indicated by numeral 800 shows inhale and exhale cycles (e.g., three complete cycles) captured during the first 15 seconds of the data collection performed during testing on the setup of FIG. 6. As noted above, the inhale and exhale cycle may comprise a respiration cycle.

As shown, the inhale and exhale periods may be observed within the frequency band 802 (e.g., 50-800 Hz). After the spectrogram is computed, the frequency entropy for each window Si may be calculated using the non-normalized Shannon entropy criteria. Entropy may be used as a measure of energy (or activity) of the signal in the frequency domain that may be present at a given time i. Entropy of the frequency window Si may be defined as:

$$E(S_i) = -\sum_{i=1}^{n} S_i^2 \cdot \log(S_i^2)$$

where E (Si) is entropy of the frequency window Si, which may represent the Fourier transform of the signal window ti, Si=F(ti). The sum considers the contribution of all frequency components analyzed in Si. The logarithmic function allows a greater entropy weight measure to signal intensity, while attenuating noise and disturbances.

Figure 9:
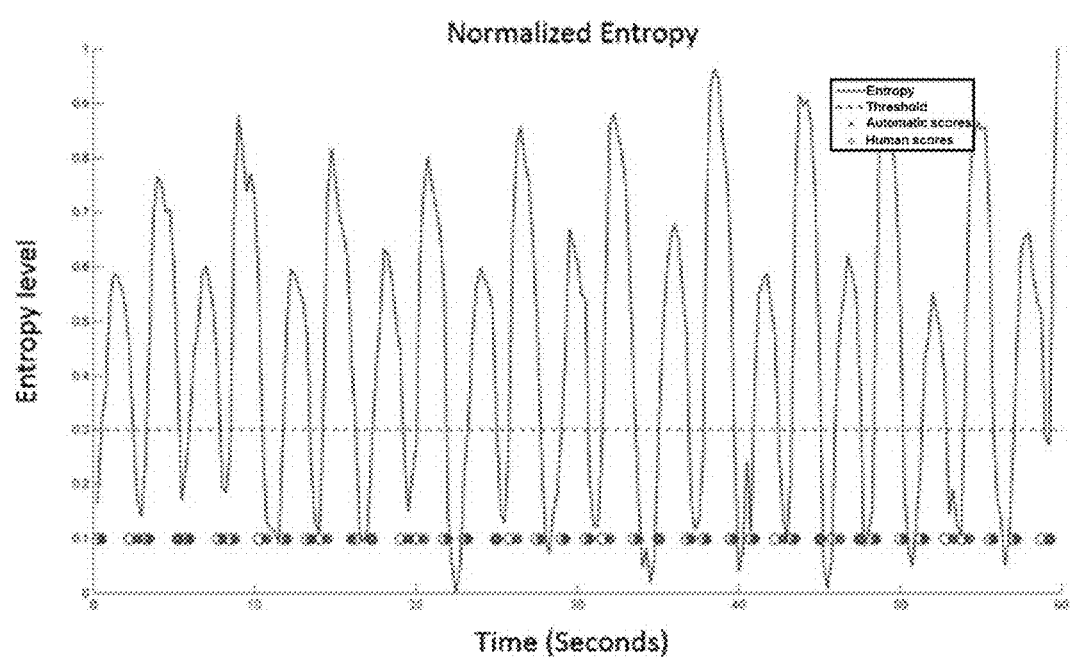
FIG. 9 is a graph illustrating example normalized entropy calculated for the spectrogram of FIG. 8, in accordance with some embodiments.

FIG. 9 is a graph illustrating example normalized entropy calculated for the spectrogram of FIG. 8, in accordance with some embodiments. An empiric threshold may be set to score the beginning and the end of an inhale or exhale cycle, or the combination of two subsequent cycles that represent a complete respiration cycle. As shown in the graph, the threshold may be set around 0.3, for example. Based on the scores, it may be possible to calculate average breathing cycle duration and/or the average number of respiration cycles per minute in real time.

To validate the performance of the process described in reference to FIGS. 6-8, the calculated scores may be compared to the scores of a human rater, to determine a correlation between the human rater-produced inhale and exhale cycle and inhale and exhale cycles determined according to the process described above. The markers at the bottom of the graph of FIG. 9 indicate manual scores of the beginning and end of a respiration inhale and exhale period, scored by a human rater (light dots) and the respiration detection according to the embodiments described herein (dark dots). The comparison metric to use may include, for example, Intra-class Correlation Coefficients (ICC), which may be suitable for continuous and ordered data. The experimental ICC results between the human rater and the automatic scores from the proposed methodology may result in an ICC equal to 0.98. The respiration cycle determination process is described in detail in reference to FIG. 11.

Figure 10:
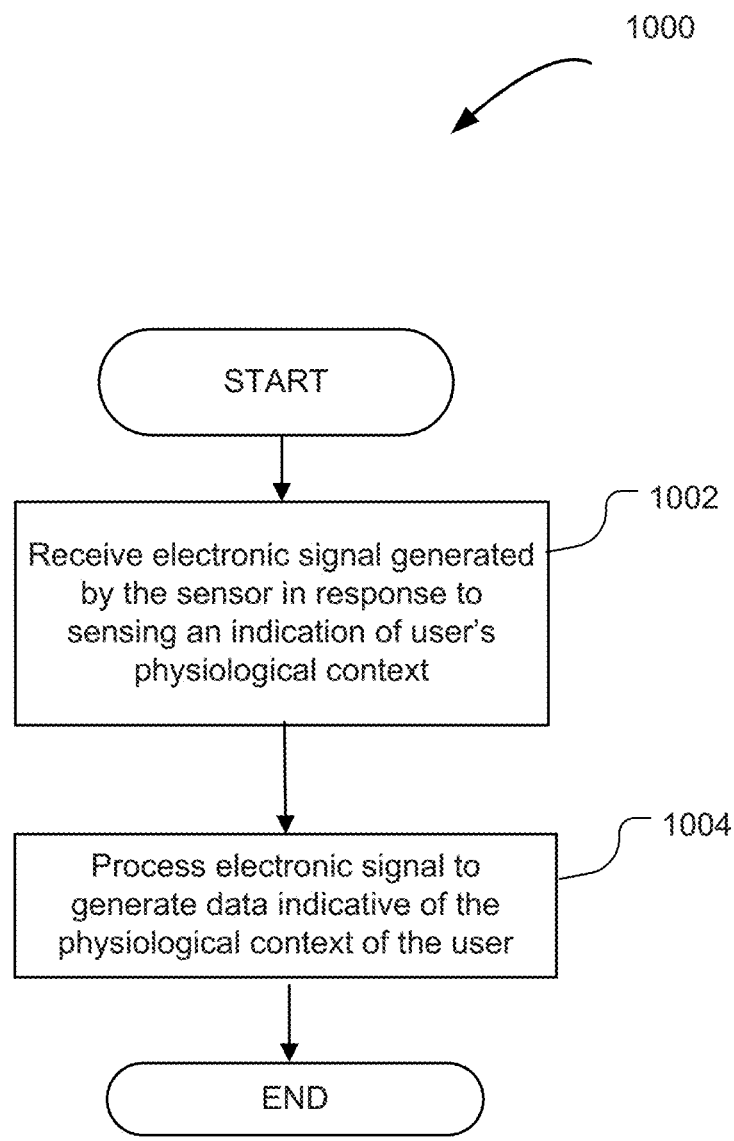
FIG. 10 is an example process flow diagram for providing measurements of the user's physiological context, in accordance with some embodiments.

FIG. 10 is an example process flow diagram for providing measurements of the user's physiological context, in accordance with some embodiments. The process 1000 may comport with some of the apparatus embodiments described in reference to FIGS. 1-9. For example, the apparatus may comprise a wearable device 101 of FIG. 1 or wearable devices 302, 312, or 332 of FIG. 3. In alternate embodiments, the process 1000 may be practiced with more or fewer operations, or a different order of the operations.

The process 1000 may begin at block 1002 and include receiving, by a controller (e.g., the earlier described controller disposed on a wearable device), from at least one sensor coupled with the controller and disposed on a head-fitting component of the wearable device, signals generated by the sensor in response to sensing an indication of the user's physiological context on a portion of the user's head. As discussed above, physiological context may include a respiration cycle, and an indication of the user's physiological context may include vibration produced in the portion of the user's head in response to the respiration cycle. The actions of block 1002 may further include recording the signal during one or more respiration cycles.

As further described above, physiological context of the user may further include temperature, and the detection of physiological context may be performed using a piezoelectric sensor with a thermocouple as described in reference to FIGS. 4-5. The actions of block 1002 may further include recording another signal provided by the sensor configured as described in reference to FIGS. 4-5, in response to sensing the temperature around the portion of the user's head.

At block 1004, the process 1000 may include processing the signal (or signals), to generate data indicative of the physiological context of the user. As described in reference to FIGS. 6-9, for respiration determination, processing may include obtaining a spectrogram of the signal and calculating entropy of the spectrogram to produce inhale and exhale cycle data, to define the respiration cycle, and determining the respiration cycle. The processing of the signal for respiration cycle determination is described in more detail in reference to FIG. 11.

Processing may further include determining the temperature of the user's body based on the other signal provided by the thermocouple of the sensor. In embodiments, the data indicative of the physiological context of the user may be provided to an external device for processing.

Figure 11:
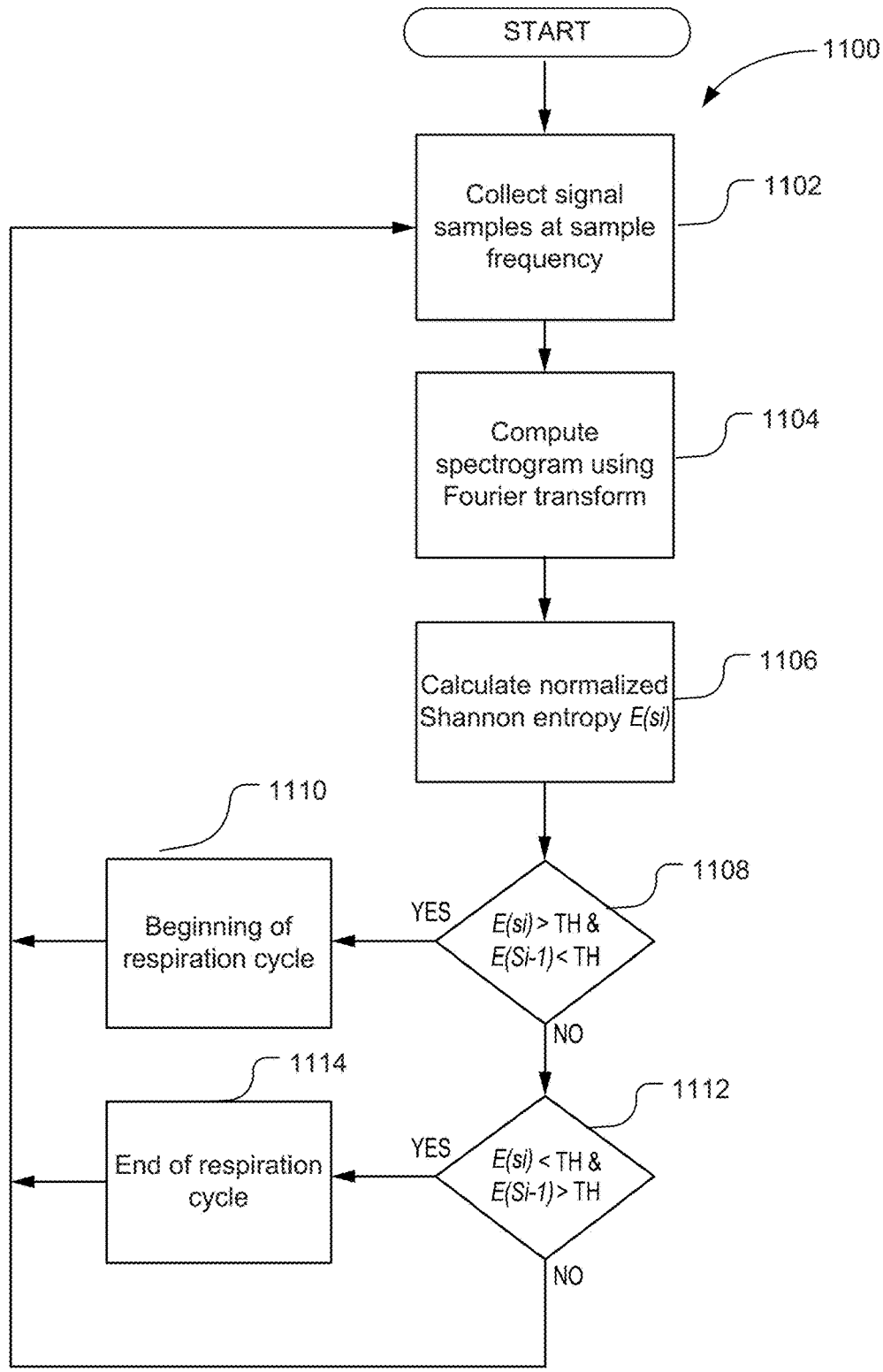
FIG. 11 is an example process flow diagram for processing the signal provided by a sensor of an apparatus for providing measurements of the user's physiological context, such as the user's respiration cycle, in accordance with some embodiments.

FIG. 11 is an example process flow diagram for processing the signal provided by a sensor of an apparatus for the user's physiological context measurements, such as the user's respiration cycle, in accordance with some embodiments. The process 1100 describes in more detail the actions of block 1002 of FIG. 10 as they relate to determining the respiration cycle of the user described in reference to FIGS. 7-9.

The process 1100 may begin at block 1102 and include collecting signal samples e.g., amplitude samples from the piezoelectric signal shown in the graph of FIG. 7 at a particular sample frequency. The sample frequency of signals shown in FIG. 7 may be, for example, about 16 kHz. In other words, data collection from the signal may occur every $1/16{,}000$ of a sec, where 16,000 samples compose 1 second of the signal. A time period of 250 ms of the signal translates into 4,000 samples enclosed in a time window ti, where i=1, 2, 3 . . . , n are the signal windows to process.

At block 1104, the process 1100 may include computing spectrogram (shown in FIG. 8) using short-time Fourier transform. A Fourier transform is a representation of the frequency components (spectrum) of a signal in the frequency domain, as opposed to the temporal domain. A spectrogram is a temporal representation of the spectrum where it may be observed how the frequency components of the window ti change over time. For the purposes of the present disclosure, the spectrogram may provide a visualization feature to identify in which frequency bands (and time periods) the indications of respiration may be taking place.

At block 1106, the process 1100 may include calculating, based on the spectrogram calculated at block 1104, normalized Shannon entropy E(si) of a window Si, in which the frequency of the signals may be observed. As discussed in reference to FIG. 9, the spectrogram may be composed of a number of windows Si. The Shannon entropy may be a measure of energy contained in the signal captured from the piezoelectric sensor. There may be different ways to calculate the level of entropy, amplitude, energy, etc. The Shannon entropy may be chosen because it considers the variability of the overall signal equally at all frequency components under analysis.

It may be calculated how much entropy is contained in Si (e.g., the 250 ms spectrogram) using Shannon's formula. The higher the entropy, the higher may be the probability that the signal may be indicative of the user's respiration. For example, absence of detected bone vibration (e.g., complete silence) may result in zero entropy.

It may be shown experimentally that respiration may be present with values higher than 0.3 of the normalized entropy. In other words, the value of 0.3 may represent a threshold TH of entropy level to consider the signal to be indicative of a respiration cycle.

At decision block 1108, the process 1100 may include determining whether the entropy level of the window Si is higher than threshold level TH (e.g., 0.3), and the entropy level of the previous window Si-1 is lower than the threshold level TH (e.g., 0.3). If both conditions are met, it may mean that the entropy level went from low to high, which may represent the beginning of a respiration cycle. Accordingly, the process 1100 may move to block 1110, at which a marker may be produced that may indicate a start of the respiration cycle.

If at least one condition of decision block 1108 is not met, the process 1100 may move to decision block 1112, in which it may be determined whether the entropy level of the window Si is lower than threshold level TH (e.g., 0.3), and the entropy level of the previous window Si−1 is higher than the threshold level TH (e.g., 0.3). If both conditions are met, it may mean that the entropy level went from high to low, which may represent the ending of a respiration cycle. Accordingly, the process 1100 may move to block 1114, at which a marker may be produced that may indicate an end of the respiration cycle. Thus, the process 1100 may identify a respiration cycle of a user based on processing of the signal provided by the sensor of the apparatus for determining the user's respiration cycle.

The following paragraphs describe examples of various embodiments.

Example 1 may be an apparatus for a user's physiological context measurements, comprising: a head-fitting component to be mounted at least partly around a user's head; at least one sensor disposed on the head-fitting component to generate a signal indicative of a user's physiological context in response to contact with the user's head, wherein the physiological context comprises a respiration cycle, wherein the sensor is to sense vibration in a portion of the user's head produced in response to the respiration cycle; and a controller coupled with the at least one sensor, to process the signal and generate data indicative of the physiological context of the user.

Example 2 may include the subject matter of Example 1, wherein the head-fitting component is to provide the contact between the sensor and the portion of the user's head, in response to application of the apparatus to the user's head, wherein the apparatus comprises a wearable device.

Example 3 may include the subject matter of Example 2, wherein the controller to generate data indicative of the physiological context of the user is to provide information indicative of an inhale cycle and exhale cycle that define the respiration cycle of the user.

Example 4 may include the subject matter of Example 3, wherein the controller to provide information indicative of the respiration cycle of the user includes to record the signal during one or more respiration cycles, and to provide or cause to be provided analysis of the signal, which includes to obtain a spectrogram of the signal and calculate entropy of the spectrogram to produce inhale and exhale cycle indications.

Example 5 may include the subject matter of Example 2, wherein the at least one sensor comprises a piezoelectric transducer responsive to vibration.

Example 6 may include the subject matter of Example 5, wherein the physiological context of the user further comprises temperature, wherein the at least one sensor is to further sense the temperature around an area of the at least a portion of the user's head.

Example 7 may include the subject matter of Example 6, wherein the piezoelectric transducer includes a piezoelectric disc with first and second electrical contacts coupled with the disc, wherein one of the first or second electrical contacts comprises a thermocouple.

Example 8 may include the subject matter of Example 6, wherein the controller to generate data indicative of the physiological context of the user is to further provide information indicative of the temperature of the user.

Example 9 may include the subject matter of Example 1, wherein the apparatus comprises eyeglasses, wherein the head-fitting component comprises a frame with a nosepiece, wherein the portion of the user's head comprises a nose, wherein the sensor is mounted or removably attached on the nosepiece.

Example 10 may include the subject matter of Example 1, wherein the apparatus comprises eyeglasses, wherein the head-fitting component comprises a frame, wherein the portion of the user's head comprises a temple, wherein the sensor is mounted or removably attached on a side of the frame that is placed adjacent to the temple, in response to application of the eyeglasses to the user's head.

Example 11 may include the subject matter of Example 1, wherein the apparatus comprises one of: a helmet, a headset, or a patch, wherein the head-fitting component comprises a portion of the apparatus to provide a contact between the at least one sensor and an area of an upper portion of the user's head, wherein the upper portion comprises a temple, a forehead, or a nose.

Example 12 may include the subject matter of Example 1, wherein the controller is mounted on the apparatus.

Example 13 may include the subject matter of any of Examples 1 to 12, wherein the controller includes a processing block to process the signal and generate data indicative of the physiological context of the user, and a communication block to transmit the data to an external device.

Example 14 may be a method for providing an apparatus for a user's physiological context measurements, comprising: disposing at least one sensor on a head-fitting component of a wearable device to provide a contact between the sensor and at least a portion of a user's head, wherein the at least one sensor is to generate a signal in response to sensing an indication of the user's physiological context, based on the contact with the portion of the user's head; and electrically coupling the at least one sensor with a controller, to process the signal and generate data indicative of the user's physiological context.

Example 15 may include the subject matter of Example 14, wherein the wearable device comprises eyeglasses, wherein the head-fitting component comprises a frame with a nosepiece, wherein disposing at least one sensor on a head-fitting component includes mounting the sensor on at least one of: the nosepiece or a side of the frame that is placed adjacent to an upper portion of the user's head in response to application of the eyeglasses to the user's head.

Example 16 may include the subject matter of Example 14, wherein the wearable device comprises one of: a helmet, a headset, or a headwear, wherein disposing at least one sensor on a head-fitting component includes mounting the sensor on the head-fitting component to provide a contact between the at least one sensor and an upper portion of the user's head.

Example 17 may include the subject matter of Example 14, further comprising: providing the at least one sensor, wherein the sensor comprises a piezoelectric transducer responsive to vibration.

Example 18 may include the subject matter of Example 17, wherein providing the at least one sensor includes attaching a thermocouple to the piezoelectric transducer.

Example 19 may be a method for providing a user's physiological context measurements, comprising: receiving, by a controller disposed on a wearable device, from at least one sensor coupled with the controller and disposed on the wearable device, a signal indicative of a user's physiological context and generated by the sensor in response to contact with a portion of the user's head, wherein the physiological context comprises a respiration cycle, which causes vibration in the portion of the user's head that is sensed by the sensor; and processing, by the controller, the signal, to generate data indicative of the physiological context of the user.

Example 20 may include the subject matter of Example 19, further comprising: recording, by the controller, the signal during one or more respiration cycles, wherein processing the signal includes providing or causing to be provided, by the controller, analysis of the signal, including obtaining a spectrogram of the signal and calculating entropy of the spectrogram to produce inhale and exhale cycle data, to define the respiration cycle.

Example 21 may include the subject matter of Example 20, wherein the physiological context of the user further comprises temperature, wherein the signal is a first signal, wherein the method further comprises: recording, by the controller, a second signal provided by the at least one sensor, in response to sensing the temperature around the portion of the user's head; and determining or causing to be determined, by the controller, the temperature based on the second signal.

Example 22 may include the subject matter of any of Examples 19 to 21, further comprising: providing, by the controller, the data indicative of the physiological context of the user to an external device for processing.

Example 23 may be an apparatus for a user's physiological context measurements, comprising: means for receiving, from at least one sensor coupled with the controller and disposed on a wearable device, a signal indicative of a user's physiological context and generated by the sensor in response to contact with a portion of the user's head, wherein the physiological context comprises a respiration cycle, which causes vibration in the portion of the user's head that is sensed by the sensor; and means for processing the signal, to generate data indicative of the physiological context of the user.

Example 24 may include the subject matter of Example 23, further comprising: means for recording the signal during one or more respiration cycles, wherein means for processing the signal includes means for providing or causing to be provided analysis of the signal, including means for obtaining a spectrogram of the signal and calculating entropy of the spectrogram to produce inhale and exhale cycle data, to define the respiration cycle.

Example 25 may include the subject matter of Example 24, wherein the physiological context of the user further comprises temperature, wherein the signal is a first signal, wherein the apparatus further comprises: means for recording a second signal provided by the at least one sensor, in response to sensing the temperature around the portion of the user's head; and means for determining or causing to be determined the temperature based on the second signal.

Various operations are described as multiple discrete operations in turn, in a manner that is most helpful in understanding the claimed subject matter. However, the order of description should not be construed as to imply that these operations are necessarily order dependent. Embodiments of the present disclosure may be implemented into a system using any suitable hardware and/or software to configure as desired.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims and the equivalents thereof.

What is claimed is:

1. An apparatus, comprising:
a head-fitting component to be mounted at least partly around a user's head;
at least one sensor disposed on the head-fitting component to generate a signal indicative of a user's physiological context in response to contact with the user's head, wherein the physiological context comprises a respiration cycle and a temperature of the user, wherein the sensor comprises a piezoelectric diaphragm coupled with a metal component, with first and second electrical contacts respectively coupled with the diaphragm and the metal component, wherein the second electrical contact comprises a thermocouple, wherein the diaphragm is to sense vibration in a portion of the user's head produced in response to the respiration cycle, and the thermocouple is to sense a temperature of the user; and
a controller coupled with the at least one sensor, to process the signal and generate data indicative of the physiological context of the user.

2. The apparatus of claim 1, wherein the head-fitting component is to provide the contact between the sensor and the portion of the user's head, in response to application of the apparatus to the user's head, wherein the apparatus comprises a wearable device.

3. The apparatus of claim 2, wherein the controller to generate data indicative of the physiological context of the user is to provide information indicative of an inhale cycle and exhale cycle that define the respiration cycle of the user.

4. The apparatus of claim 3, wherein the controller to provide information indicative of the respiration cycle of the user includes to record the signal during one or more respiration cycles, and to provide or cause to be provided analysis of the signal, which includes to obtain a spectrogram of the signal and calculate entropy of the spectrogram to produce inhale and exhale cycle indications.

5. The apparatus of claim 2, wherein the at least one sensor comprises a piezoelectric transducer responsive to vibration.

6. The apparatus of claim 5, wherein the physiological context of the user further comprises temperature, wherein the at least one sensor is to further sense the temperature around an area of the at least a portion of the user's head.

7. The apparatus of claim 6, wherein the controller to generate data indicative of the physiological context of the user is to further provide information indicative of the temperature of the user.

8. The apparatus of claim 1, wherein the apparatus comprises eyeglasses, wherein the head-fitting component comprises a frame with a nosepiece, wherein the portion of the user's head comprises a nose, wherein the sensor is mounted or removably attached on the nosepiece.

9. The apparatus of claim 1, wherein the apparatus comprises eyeglasses, wherein the head-fitting component comprises a frame, wherein the portion of the user's head comprises a temple, wherein the sensor is mounted or removably attached on a side of the frame that is placed adjacent to the temple, in response to application of the eyeglasses to the user's head.

10. The apparatus of claim 1, wherein the apparatus comprises one of: a helmet, a headset, or a patch, wherein the head-fitting component comprises a portion of the apparatus to provide a contact between the at least one sensor and an area of an upper portion of the user's head, wherein the upper portion comprises a temple, a forehead, or a nose.

11. The apparatus of claim 1, wherein the controller is mounted on the apparatus.

12. The apparatus of claim 1, wherein the controller includes a processing block to process the signal and generate data indicative of the physiological context of the user, and a communication block to transmit the data to an external device.

* * * * *